(12) United States Patent
Dessen et al.

(10) Patent No.: US 11,712,448 B2
(45) Date of Patent: Aug. 1, 2023

(54) USE OF ALGINATE OLIGOMERS AS BLOOD ANTICOAGULANTS

(71) Applicant: ALGIPHARMA AS, Sandvika (NO)

(72) Inventors: Arne Dessen, Røyken (NO); Philip Rye, Eiksmarka (NO)

(73) Assignee: ALGIPHARMA AS, Sandvika (NO)

( * ) Notice: Subject to any disclaimer, the term of this patent is extended or adjusted under 35 U.S.C. 154(b) by 0 days.

(21) Appl. No.: 15/106,196

(22) PCT Filed: Dec. 19, 2014

(86) PCT No.: PCT/GB2014/053808
§ 371 (c)(1),
(2) Date: Jun. 17, 2016

(87) PCT Pub. No.: WO2015/092437
PCT Pub. Date: Jun. 25, 2015

(65) Prior Publication Data
US 2016/0331777 A1 Nov. 17, 2016

(30) Foreign Application Priority Data
Dec. 20, 2013 (GB) .................................... 1322777

(51) Int. Cl.
| | | |
|---|---|---|
| A61K 31/734 | (2006.01) | |
| A61P 7/02 | (2006.01) | |
| A61K 31/702 | (2006.01) | |
| A61M 1/36 | (2006.01) | |
| A61L 33/08 | (2006.01) | |
| A61K 31/715 | (2006.01) | |

(52) U.S. Cl.
CPC .......... *A61K 31/734* (2013.01); *A61K 31/702* (2013.01); *A61K 31/715* (2013.01); *A61L 33/08* (2013.01); *A61M 1/3673* (2014.02); *A61P 7/02* (2018.01)

(58) Field of Classification Search
CPC . A61K 31/715; A61K 31/734; A61M 1/3673; A61L 33/08; C08L 5/04
USPC ........................................................ 514/54
See application file for complete search history.

(56) References Cited

U.S. PATENT DOCUMENTS

| | | | |
|---|---|---|---|
| 2,508,433 A | 5/1950 | Snyder | |
| 5,135,955 A * | 8/1992 | Campbell ............. | C07C 211/27 514/649 |
| 5,415,619 A | 5/1995 | Lee et al. | |
| 5,646,130 A | 7/1997 | Shi | |
| 6,121,441 A | 9/2000 | Simensen et al. | |

FOREIGN PATENT DOCUMENTS

| | | |
|---|---|---|
| CN | 1542021 A | 11/2004 |
| CN | 102212148 | 10/2011 |
| CN | 102382204 A | 3/2012 |
| CN | 103142539 A | 6/2013 |
| EP | 0 059 221 A1 | 9/1982 |
| KR | 20110133917 A | 12/2011 |
| WO | WO 94/09124 A1 | 4/1994 |
| WO | WO 2004/011628 A1 | 2/2004 |
| WO | WO 2005/023176 A2 | 3/2005 |
| WO | WO 2007/039754 A1 | 4/2007 |
| WO | WO 2007/039760 A2 | 4/2007 |
| WO | WO 2008/073670 A2 | 6/2008 |
| WO | WO 2008/125828 A2 | 10/2008 |
| WO | WO 2009/068841 A2 | 6/2009 |
| WO | WO 2009/103977 A1 | 8/2009 |
| WO | WO 2010/139957 A2 | 12/2010 |

OTHER PUBLICATIONS

Subaryono et al. (Squalen Bulletin of Marine & Fisheries Postharvest & Biotechnology, 8 (3), 2013, 105-116).*
Cordoba et al. (Transfusion and Apheresis Science 48 (2013) 301-305).*
Lin et al., "The influence of molecular mass of sulfated propylene glycol ester of low-molecular-weight alginate on anticoagulant activities" European Polymer Journal vol. 43 pp. 3009-3015 doi:10. 1016/j.eurpolymj.2007.04.015 (Year: 2007).*
Ronghua et al., "Preparation and in vitro anticoagulant activities of alginate sulfate and its quaterized derivatives" Carbohydrate Polymers vol. 52 pp. 19-24 (Year: 2003).*
Arlov et al. 2014 "Heparin-Like Properties of Sulfated Alginates with Defined Sequences and Sulfation Degrees" *Biomacromolecules* 15(7): 2744-2750.
Arlov, O. 2012"Heparin Analogs Created by Sulfation of Alginates Using a Chemoenzymatic Strategy" Thesis, Norwegian University of Science and Technology, Department of Biotechnology. In 84 pages.
Ertesvag, H. et al. 1999 "Mannuronan C-5-Epimerases and their application for in vitro and in vivo design of new alginates useful in biotechnology" *Metabolic Engineering* 1: 262-269.
Gao et al. 2013 "Sodium alginate/heparin composites on PVC surfaces inhibit the thrombosis and platelet adhesion: applications in cardiac surgery" *Int J Clin Exp Med* 6(4):259-268.
Gimmestad, M. et al. 2003 "The *Pseudomonas fluorescens* AlgG protein, but not its mannuronan C-5-epimerase activity, is needed for alginate polymer formation" *J Bacteriology* 185: 3515-3523.
Gimmestad, M. et al. 2006 "Identification and Characterization of an *Azotobacter vinelandii*Type I Secretion System Responsible for Export of the AlgE-Type Mannuronan C-5-Epimerases" *J Bacteriology* 188: 5551-5560.

(Continued)

*Primary Examiner* — Eric Olson
(74) *Attorney, Agent, or Firm* — Knobbe, Martens, Olson & Bear, LLP

(57) ABSTRACT

The disclosure relates to an alginate oligomer of 2 to 75 monomer residues, wherein said monomer residues do not carry a sulphate group, for use as a blood anticoagulant in clinical and non-clinical applications, including in vivo, ex vivo and in vitro contexts. The invention further provides for the use of such an alginate oligomer in preparing a product or device having a reduced capacity to promote blood coagulation, wherein said alginate oligomer is provided at or on a surface of said product or device. Such products and devices form a further aspect of the invention.

35 Claims, No Drawings

(56) References Cited

OTHER PUBLICATIONS

Keuren et al. 2003 "Thrombogenicity of polysaccharide-coated surfaces" *Biomaterials* 24: 1917-1924.
Leventon, W. 2003 "Hemocompatible Coatings for Blood-Contacting Devices" Published on MDDI Medical Device and Diagnostic Industry News Products and Suppliers (on the World-Wide Web at www.mddionline.com) (in 7 pages).
Remminghorst and Rehm 2006 "Bacterial alginates: from biosynthesis to applications" *Biotechnol Lett* 28: 1701-1712.
Strugala et al. 2004 "Bioactive properties of epimerized alginates" in Gums and Stabilizers for the Food Industry 12, The Royal Society of Chemistry, Editors: Glyn O Phillips, Peter A Williams, pp. 84-94.
Surmodics 2014 "Hemocompatible coatings" (available on the World-Wide-Web at surmodics.com/medical-device/coating-technologies/hemocompatible-coatings-overview/hemocompatible-coatings-technology/).
Yoshida et al. 2000 "Specific biological activities of Chinese lacquer polysaccharides" *Carbohydrate Polymers* 43: 47-54.
Yoshioka, et al. 2003 "Blood compatibility of stainless-steel and titanium immobilized with alginic acid layers" *Materials Research Society Symp Proc* 734: 333-338.
Yoshioka, et al. 2003 "Preparation of alginic acid layers on stainless-steel substrates for biomedical applications" *Biomaterials* 24(17): 2889-2894.
Karakai, N. et al. 2013 "The antioxidant and anticoagulant activities of polysaccharides isolated from the brown algae *Dictyopteris polypodioides* growing on the Lebanese coast" *Journal of Applied Pharmaceutical Science* vol. 3 (02): 043-051.
Matsubara, K. 2004 "Recent Advances in Marine Algal Anticoagulants" *Curr Med Chem* 2: 13-19.
Shobharani, P. et al. 2014 "Antioxidant and anticoagulant activity of polyphenol and polysaccharides from *Sargassum* sp." *International Journal of Biological Macromolecules* 65: 542-548.
Sokolova, E.V. et al. 2013 "Influence of red algal sulfated polysaccharides on blood coagulation and platelets activation in vitro" *J Biomed Mater Res Part A* 102A: 1431-1438.
Zhao et al. 2007 "Preparation of low-molecular-weight polyguluronate sulfate and its anticoagulant and anti-inflammatory activities" *Carbohydrate Polymers* 69: 272-279.
Office Action in corresponding Chinese Application No. 201480074815.2, dated Jul. 2, 2019.
Zhang, W. et al. 2014 "Electrophoretic Separation of Alginic Sodium Diester and Sodium Hexametaphosphate in Chondroitin Sulfate that Interfere with the Cetylpyridinium Chloride Titration Assay" Journal of AOAC International vol. 97, No. 6: (in 11 pages).
Zheng, Z. 1997 "Changes to Nailfold Microcirculation after Application of Alginic Sodium Diester to Patients of Nephrotic Syndrome" Jiangsu Medical Journal, 1997, vol. 23, No. 1 (in 4 pages).
Nishimujra et al. "Inhibition of the hydrolytic activity of thrombin by chitin heparinoids" *Carbohydrate Research*, 156:286-292(1986).
Guo et al. "Complete Genome of Pseudomonas mendocina NK-01, Which Synthesizes Medium-Chain-Length Polyhydroxyalkanoates and Alginate Oligosaccharides" *Journal of Bacteriology*, 193(13):3413-3414 (2011).
Lin et al. "The influence of molecular mass of sulfated propylene glycol ester of low-molecular-weight alginate on anticoagulant activities" *European Polymer Journal* 43:3009-3015 (2007).
Szekalska et al. "Alginate: Current Use and Future Perspectives in Pharmaceutical and Biomedical Applications" *International Journal of Polymer Science* vol. 2016, Article ID 7697031 (2016), in 17 pages.

\* cited by examiner

USE OF ALGINATE OLIGOMERS AS BLOOD ANTICOAGULANTS

FIELD OF THE INVENTION

The present invention relates to the use of alginate oligomers as blood anticoagulants, that is agents capable of preventing or inhibiting the formation of fibrin clots in whole blood or plasma. Accordingly the invention provides a method for preventing or inhibiting blood coagulation and thereby regulating blood coagulation. The need to regulate or control blood clotting arises in clinical and non-clinical contexts. The methods of the invention may therefore be applied in the therapeutic and surgical management of diseases and conditions associated with unwanted blood coagulation (thrombosis) but also in the handling of whole blood, plasma or compositions containing the same and also of materials, products or devices, or parts thereof, which when in use come into contact with blood or a blood-derived product. Products and devices adapted for use in such applications containing and/or coated with alginate oligomers are also provided.

BACKGROUND OF THE INVENTION

Blood coagulation (or blood clotting, which terms are used interchangeably herein) is a physiological mechanism evolved by vertebrates to counteract and remedy injury to the circulatory system. Put simply, the blood coagulation process results in the production of an aggregated mass of cells and proteinaceous matrix that physically plugs the breech in the integrity of the circulatory system caused by the injury.

More specifically the in vivo coagulation process is a complex bifurcated cascade of proteolytic reactions that results in the conversion of fluid blood to a solid gel ultimately through the conversion soluble fibrinogen to insoluble fibrin. The conversion of fibrinogen to fibrin results in a matrix of proteinaceous filaments which trap blood cells and other blood components. Regardless of the exact makeup of the resulting entity, it is referred to as a blood clot or clinically as a thrombus.

The in vivo coagulation process is bifurcated in that there are two recognised different initiation points which converge at the point of Factor X, the protein which converts prothrombin to thrombin, which in turn catalyses the conversion of fibrinogen to fibrin. One of the bifurcated coagulation pathways is referred to as the "intrinsic pathway" or the "contact activation pathway" on account of initial observations that the pathway was activated upon contact of blood with artificial surfaces. By definition the essential mediators of this process are all present in the blood, hence "intrinsic". The other bifurcated coagulation pathway is referred to as the "extrinsic pathway" or "tissue factor pathway" on account of the requirement for initiation by an extraneous cell surface mediator "tissue factor". Tissue factor exposure occurs immediately upon tissue injury and hence the extrinsic pathway is viewed as the dominant pathway in vivo.

Although blood coagulation is an essential defence mechanism of vertebrate organisms against injury, unwanted or inappropriate coagulation in a clinical context gives rise to thrombotic diseases in which a blood clot causes an obstruction in a blood vessel or the heart. Such events often lead to hypoxia and even infarction in the downstream tissues. Tissue or organ damage may ensue and depending on the location of the ischemia, the thrombosis or resulting tissue damage may manifest as conditions such as hypertension, low blood oxygenation, stroke, cardiac infarction, pulmonary embolism and angina.

The existence of the contact activation pathway, which is independent of tissue-based mediators, means coagulation of whole blood is observed in vitro. Moreover, products containing the clotting factors of whole blood, e.g. plasma, can display coagulation, even if such products are devoid of cells and/or platelets. In these embodiments insoluble fibrin networks will form, although in the absence of blood cells the overall appearance of the clots will differ from those formed in whole blood. Accordingly the blood coagulation pathway is also important in the context of the handling of blood and blood products in vitro.

Pharmaceutical interventions which treat or prevent thrombotic diseases are available but are limited in number and have issues of toxicity, drug interactions and dosing and restrictions on routes delivery. Alternative anticoagulants that have a better safety profile, that are easier to dose and with fewer restrictions on administration routes are desired. Further, it is known to provide materials, products or devices, or parts thereof, which when in use come into contact with blood or a blood-derived product with surfaces, e.g. surface coatings, comprising haemocompatible compounds designed to minimise blood coagulation at those surfaces. Alternative, preferably improved, haemocompatible compounds for use as or in such surface coatings are desired. Additives to counteract coagulation in vitro are also available, although alternatives are always required, especially alternatives that are safe to use with blood products intended to be administered to human or non-human animal subjects.

Alginates are naturally occurring polysaccharides that have been found to have a number of uses, both clinical (e.g. in wound dressings, as drug carriers and in anti-heartburn preparations) and non-clinical (e.g. in food preparation). They are linear polymers of (1-4) linked β-D-mannuronic acid (M) and/or its C-5 epimer α-L-guluronic acid (G). The primary structure of alginates can vary greatly. The M and G residues can be organised as homopolymeric blocks of contiguous M or G residues, as blocks of alternating M and G residues and single M or G residues can be found interspacing these block structures. An alginate molecule can comprise some or all of these structures and such structures might not be uniformly distributed throughout the polymer. In the extreme, there exists a homopolymer of guluronic acid (polyguluronate) or a homopolymer of mannuronic acid (polymannuronate).

Alginates have been isolated from marine brown algae (e.g. certain species of *Durvillea*, *Lessonia* and *Laminaria*) and bacteria such as *Pseudomonas aeruginosa* and *Azotobacter vinelandii*. Other pseudomonads (e.g. *Pseudomonas fluorescens*, *Pseudomonas putida*, and *Pseudomonas mendocina*) retain the genetic capacity to produce alginates but in the wild they do not produce detectable levels of alginate. By mutation these non-producing pseudomonads can be induced to produce stably large quantities of alginate.

Alginate is synthesised as polymannuronate and G residues are formed by the action of epimerases (specifically C-5 epimerases) on the M residues in the polymer. In the case of alginates extracted from algae, the G residues are predominantly organised as G blocks because the enzymes involved in alginate biosynthesis in algae preferentially introduce the G neighbouring another G, thus converting stretches of M residues into G-blocks. Elucidation of these biosynthetic systems has allowed the production of alginates with specific primary structures (WO 94/09124, Gimmestad, M et al, Journal of Bacteriology, 2003, Vol 185(12) 3515-3523 and WO 2004/011628).

Alginates are typically isolated from natural sources as large high molecular weight polymers (e.g. an average molecular weight in the range 300,000 to 500,000 Daltons). It is known, however, that such large alginate polymers may be degraded, or broken down, e.g. by chemical or enzymatic hydrolysis to produce alginate structures of lower molecular weight. Alginates that are used industrially typically have an average molecular weight in the range of 100,000 to 300,000 Daltons (such alginates are still considered to be large polymers) although alginates of an average molecular weight of approximately 35,000 Daltons have been used in pharmaceuticals.

SUMMARY OF THE INVENTION

More recently alginate oligomers of smaller size (molecular weight) have been proposed for clinical use, most notably to reduce the viscosity of mucus, including in particular hyperviscous mucus such as occurs in sufferers of cystic fibrosis and other respiratory diseases (see WO 2007/039754 and WO 2008/125828) or anti-microbially, against biofilm (WO 2009/068841) and multidrug resistant bacteria (WO 2010/13957).

It has now unexpectedly been found that alginate oligomers, specifically non-sulphated alginate oligomers of 2 to 75 monomers, can inhibit and even prevent the coagulation of blood and thereby regulate and control blood coagulation, and as a result it is proposed that such alginate oligomers be used as blood anticoagulants in methods for preventing or inhibiting blood coagulation in whole blood or compositions, e.g. blood products, containing blood clotting factors in any context outside or inside the human or animal body. Such contexts may include the inhibition or prevention of blood coagulation on or in any materials, products or devices which when in use, whether outside or inside the human or animal body, come into contact with blood or a blood-derived product. In such aspects the alginate oligomer may be provided at or on the surface of such materials, products or devices (i.e. in an immobilised form). Alginate oligomers are readily amenable to being provided in such forms. Such contexts also include harnessing the anticoagulant effects of alginate oligomers in the human or animal body as anticoagulant therapeutic agents, which may be provided in a non-immobilised form. Alginate oligomers are non-toxic, easy to administer and dose and are not known to display drug interactions and, as such, these compounds address some or all of the various deficiencies noted above.

Accordingly, in a first aspect the invention provides a method for the prevention or inhibition of blood coagulation, said method comprising contacting a composition comprising blood plasma, preferably whole blood, or a material with which said composition is, or may be, in contact, with an alginate oligomer of 2 to 75 monomer residues, wherein said monomer residues do not carry a sulphate group.

The term "contacting" encompasses any means of delivering the alginate oligomer to the composition comprising blood plasma (or exposing the composition to the alginate oligomer), whether directly or indirectly. The alginate may be provided in a free and/or an immobilised form, e.g. carried on or contained in a surface which when in use may come into contact with the composition comprising blood plasma. Alginate oligomers may be applied to or incorporated into the material from which the surface is formed or the material may be impregnated with the oligomer, e.g. alginate oligomers may be coated onto a surface of the material, or provided as part of a surface coating. This may occur before, during or after formation of the surface and may be effected through covalent or non-covalent interactions, e.g. ionic or electrostatic interactions, or, expressed more generally, by adsorption, which may be in any manner. In particular, alginate oligomers of suitable monomer composition may be provided on a surface as a, or part of a, cation-induced gel.

The alginate oligomers of the invention, when provided at or on the surface of a material render that material more haemocompatible and thus, in certain embodiments, may be considered to be a haemocompatible layer or coating.

In still further embodiments the alginate oligomer is provided or included in a haemocompatible coating comprising one or more further haemocompatible compounds, e.g. heparin, heparan sulphate, hyaluronan, polyethylene glycol or dextran, or indeed any bioactive agent which has an anticoagulant activity or property or any agent or material which assists in reducing coagulation, e.g. reducing platelet activation and/or binding of blood components (e.g. proteins) required for coagulation.

In other embodiments the alginate oligomer is not used in an immobilised form. Typically in such embodiments the alginate oligomer is administered in its native form or as part of a composition, e.g. pharmaceutically acceptable formulation.

In particular, the step of contacting the composition with the alginate oligomer may include administering the alginate oligomer to a subject, and in particular to a subject in need of such treatment (e.g. a subject at risk of thrombosis, or a subject in which thrombosis is occurring or has occurred or is suspected to be occurring or to have occurred (i.e. in which a thrombus is forming or has formed or is suspected to be forming or to have formed).

The invention may be thus be used to inhibit or prevent blood coagulation in any context outside of the human or animal body, in particular on or in any materials, products or devices which when in use in vitro or ex vivo come into contact with blood or a blood-derived product, but in further aspects the anticoagulation effects of alginate oligomers are harnessed in the context of the human or animal body, e.g. as therapeutic agents or as a part of engineered surfaces of implantable or in-dwelling medical devices. It will be appreciated therefore that both medical and non-medical methods are included, e.g. in vitro and ex vivo methods are included as well as in vivo methods. As explained in more detail below, expressly included within the scope of the invention are methods which are not carried out in or on the human or non-human animal body, or in relation to, or in or on a device or material wholly or partly contained in or on the human or non-human vertebrate body.

Thus the invention provides an alginate oligomer for use as a therapeutic blood anticoagulant, wherein said alginate oligomer contains 2 to 75 monomer residues, and said monomer residues do not carry a sulphate group. Put differently, the invention provides an alginate oligomer for use as an antithrombotic agent, wherein said alginate oligomer contains 2 to 75 monomer residues, and said monomer residues do not carry a sulphate group.

The invention further provides an alginate oligomer for use in anticoagulation (or antithrombosis) therapy, wherein said alginate oligomer contains 2 to 75 monomer residues, and said monomer residues do not carry a sulphate group. More specifically, the invention provides an alginate oligomer for use in a method for treating or preventing thrombosis, or a disease or condition associated with blood coagulation (or thrombosis), wherein said alginate oligomer contains 2 to 75 monomer residues, and said monomer residues do not carry a sulphate group.

In a further aspect the invention provides an alginate oligomer for the manufacture of a medicament for use in blood anticoagulation (or antithrombosis) therapy, wherein said alginate oligomer contains 2 to 75 monomer residues, and said monomer residues do not carry a sulphate group. More specifically, the invention provides an alginate oligomer for the manufacture of a medicament for use in a method of treating or preventing thrombosis, or a disease or condition associated with blood coagulation (thrombosis), wherein said alginate oligomer contains 2 to 75 monomer residues, and said monomer residues do not carry a sulphate group.

Thus the invention also provides a method of anticoagulation (or antithrombosis) therapy said method comprising administering an alginate oligomer to a human or non-human vertebrate subject in need of said therapy, wherein said alginate oligomer contains 2 to 75 monomer residues, and said monomer residues do not carry a sulphate group.

Thus the invention also provides a method for treating or preventing thrombosis, or a disease or condition associated with blood coagulation (or thrombosis), said method comprising administering an alginate oligomer to a human or non-human vertebrate subject in need thereof, wherein said alginate oligomer contains 2 to 75 monomer residues, and said monomer residues do not carry a sulphate group.

In these therapeutic embodiments the alginate oligomer is administered in an amount effective to inhibit or prevent blood coagulation, e.g. to treat or prevent the target disease or condition associated with blood coagulation.

The therapeutic methods of the invention may be preceded by a step in which the subject is identified or diagnosed as a subject at risk of thrombosis, or a subject in which a thrombus is forming or has formed or is suspected to be forming or to have formed, e.g. a subject having, suspected to have, or at risk of a disease or condition associated with blood coagulation.

In other embodiments the therapeutic methods of the invention may be followed by a step in which the subject is monitored for an effect on the thrombosis and/or a change in condition or clinical status. For example, the subject is monitored for the formation of a blood clot, or number of clots, and/or an existing blood clot is monitored for changes in size, shape and/or integrity, e.g. using the techniques detailed below. In other embodiments the additional step may be a step in which the subject is monitored for onset of a disease or condition associated with blood coagulation or changes in a pre-existing disease or condition associated with blood coagulation. In other embodiments the additional step may be a step in which the subject's blood is tested to assess its capacity to coagulate, e.g. using the coagulation tests detailed below.

DETAILED DESCRIPTION OF CERTAIN EMBODIMENTS OF THE INVENTION

As noted above, alginates typically occur as polymers of an average molecular weight of at least 35,000 Daltons, i.e. approximately 175 to approximately 190 monomer residues, although typically much higher and an alginate oligomer according to the present invention may be defined as a material obtained by fractionation (i.e. size reduction) of an alginate polymer, commonly a naturally occurring alginate. More particularly an alginate oligomer for use according to the invention will contain 2 to 75, preferably 2 to 50, more preferably 2 to 40, 2 to 35 or 2 to 30 residues. Thus, an alginate oligomer for use according to the invention will typically have an average molecular weight of 350 to 15,000 Daltons, preferably 350 to 10,000 Daltons and more preferably 350 to 8000 Daltons, 350 to 7000 Daltons, or 350 to 6,000 Daltons.

Alternatively put, the alginate oligomer may have a degree of polymerisation (DP), or a number average degree of polymerisation (DPn) of 2 to 75, preferably 2 to 50, more preferably 2 to 40, 2 to 35, 2 to 30, 2 to 28, 2 to 25, 2 to 22, 2 to 20, 2 to 18, 2 to 17, 2 to 15 or 2 to 12.

Other representative ranges (whether for the number of residues, DP or DPn) include any one of 3, 4, 5, 6, 7, 8, 9, 10 or 11 to any one of 50, 45, 40, 39, 38, 37, 36, 35, 34, 33, 32, 31, 30, 29, 28, 27, 26, 25, 24, 23, 22, 21, 20, 19, 18, 17, 16, 15, 14, 13 or 12.

Other representative ranges (whether for the number of residues, DP or DPn) include any one of 8, 9, 10, 11, 12, 13, 14 or 15 to any one of 50, 45, 40, 39, 38, 37, 36, 35, 34, 33, 32, 31, 30, 29, 28, 27, 26, 25, 24, 23, 22, 21, 20, 19, 18, 17 or 16.

Other representative ranges (whether for the number of residues, DP or DPn) include any one of 11, 12, 13, 14, 15, 16, 17 or 18 to any one of 50, 45, 40, 39, 38, 37, 36, 35, 34, 33, 32, 31, 30, 29, 28, 27, 26, 25, 24, 23, 22, 21, 20 or 19.

An alginate oligomer will, as noted above, contain (or comprise) guluronate or guluronic acid (G) and/or mannuronate or mannuronic acid (M) residues or units. An alginate oligomer according to the invention will preferably be composed solely, or substantially solely (i.e. consist essentially of) uronate/uronic acid residues, more particularly solely or substantially solely of G and/or M residues. Alternatively expressed, in the alginate oligomer of use in the present invention, at least 80%, more particularly at least 85, 90, 95 or 99% of the monomer residues may be uronate/uronic acid residues, or, more particularly G and/or M residues. In other words, preferably the alginate oligomer will not comprise other residues or units (e.g. other saccharide residues, or more particularly other uronic acid/uronate residues).

The alginate oligomer is preferably a linear oligomer.

More particularly, in a preferred embodiment at least 30% of the monomer residues of the alginate oligomer are G residues (i.e. guluronate or guluronic acid). In other words the alginate oligomer will contain at least 30% guluronate (or guluronic acid) residues. Specific embodiments thus include alginate oligomers with (e.g. containing) 30 to 70% G (guluronate) residues or 70 to 100% G (guluronate) residues. Thus, a representative alginate oligomer for use according to the present invention may contain at least 70% G residues (i.e. at least 70% of the monomer residues of the alginate oligomer will be G residues).

Preferably at least 50% or 60%, more particularly at least 70% or 75%, even more particularly at least 80, 85, 90, 91, 92, 93, 94, 95, 96, 97, 98 or 99% of the monomer residues are guluronate. In one embodiment the alginate oligomer may be an oligoguluronate (i.e. a homooligomer of G, or 100% G)

In a further preferred embodiment, the above described alginates of the invention have a primary structure wherein the majority of the G residues are in so called G-blocks. Preferably at least 50%, more preferably at least 70 or 75%, and most preferably at least 80, 85, 90, 92 or 95% of the G residues are in G-blocks. A G block is a contiguous sequence of at least two G residues, preferably at least 3 contiguous G residues, more preferably at least 4 or 5 contiguous G residues, most preferably at least 7 contiguous G residues.

In particular at least 90% of the G residues are linked 1-4 to another G residue. More particularly at least 95%, more preferably at least 98%, and most preferably at least 99% of the G residues of the alginate are linked 1-4 to another G residue.

The alginate oligomer of use in the invention is preferably a 3- to 35-mer, more preferably a 3- to 28-mer, in particular a 4- to 25-mer, e.g. a 5- to 20-mer, especially a 6- to 22-mer, in particular an 8- to 20-mer, especially a 10- to 15-mer, e.g. having a molecular weight in the range 350 to 6400 Daltons or 350 to 6000 Daltons, preferably 550 to 5500 Daltons, preferably 750 to 5000 Daltons, and especially 750 to 4500 Daltons or 2000 to 3000 Daltons or 900 to 3500 Daltons. Other representative alginate oligomers include, as mentioned above, oligomers with 5, 6, 7, 8, 9, 10, 11 or 12 to 50, 45, 40, 35, 28, 25, 22 or 20 residues.

It may be a single compound or it may be a mixture of compounds, e.g. of a range of degrees of polymerization. As noted above, the monomeric residues in the alginate oligomer, may be the same or different and not all need carry electrically charged groups although it is preferred that the majority (e.g. at least 60%, preferably at least 80% more preferably at least 90%) do. It is preferred that a substantial majority, e.g. at least 80%, more preferably at least 90% of the charged groups have the same polarity. In the alginate oligomer, the ratio of hydroxyl groups to charged groups is preferably at least 2:1, more especially at least 3:1.

The alginate oligomer of the invention may have a degree of polymerisation (DP), or a number average degree of polymerisation ($DP_n$), of 3-28, 4-25, 6-22, 8-20 or 10-15, or 5-18 or 7-15 or 8-12, especially 10.

The alginate oligomer of the invention may have a degree of polymerisation (DP), or a number average degree of polymerisation ($DP_n$), of 5-50, 5-40, 5-35, 5-30, 5-28, 5-25, 5-22, 5-20, 5-18, 5-16, 5-15 or 5-14.

The alginate oligomer of the invention may have a degree of polymerisation (DP), or a number average degree of polymerisation ($DP_n$), of 8-50, 8-40, 8-35, 8-30, 8-28, 8-25, 8-22, 8-20, 8-18, 8-16, 8-15 or 8-14.

The alginate oligomer of the invention may have a degree of polymerisation (DP), or a number average degree of polymerisation ($DP_n$), of 9-50, 9-40, 9-35, 9-30, 9-28, 9-25, 9-22, 9-20, 9-18, 9-16, 9-15 or 9-14.

The alginate oligomer of the invention may have a degree of polymerisation (DP), or a number average degree of polymerisation ($DP_n$), of 10-50, 10-40, 10-35, 10-30, 10-28, 10-25, 10-22, 10-20, 10-18, 10-16, 10-15 or 10-14.

The alginate oligomer of the invention may have a degree of polymerisation (DP), or a number average degree of polymerisation ($DP_n$), of 12-50, 12-40, 12-35, 12-30, 12-28, 12-25, 12-22, 12-20, 12-18, 12-16, 12-15 or 12-14.

The alginate oligomer of the invention may have a degree of polymerisation (DP), or a number average degree of polymerisation ($DP_n$), of 15-50, 15-40, 15-35, 15-30, 15-28, 15-25, 15-22, 15-20, 15-18 or 15-16.

The alginate oligomer of the invention may have a degree of polymerisation (DP), or a number average degree of polymerisation ($DP_n$), of 18-50, 18-40, 18-35, 18-30, 18-28, 18-25, 18-22 or 18-20.

Preferably the alginate oligomer of the invention is substantially free, preferably essentially free, of alginate oligomers having a degree of polymerisation outside of the ranges disclosed herein. This may be expressed in terms of the molecular weight distribution of the alginate oligomer of the invention, e.g. the percentage of each mole of the alginate oligomer being used in accordance with the invention which has a DP outside the relevant range. The molecular weight distribution is preferably such that no more than 10%, preferably no more than 9, 8, 7, 6, 5, 4, 3, 2, or 1% mole has a DP of three, two or one higher than the relevant upper limit for $DP_n$. Likewise it is preferred that no more than 10%, preferably no more than 9, 8, 7, 6, 5, 4, 3, 2, or 1% mole has a DP below a number three, two or one smaller than the relevant lower limit for $DP_n$.

Suitable alginate oligomers are described in WO2007/039754, WO2007/039760, WO 2008/125828, and WO2009/068841, the disclosures of which are explicitly incorporated by reference herein in their entirety.

Representative suitable alginate oligomers have a $DP_n$ in the range 5 to 30, a guluronate/galacturonate fraction ($F_G$) of at least 0.80, a mannuronate fraction ($F_M$) of no more than 0.20, and at least 95 mole % of DP no more than 25.

Further suitable alginate oligomers have a number average degree of polymerization in the range 7 to 15 (preferably 8 to 12), a guluronate/galacturonate fraction ($F_G$) of at least 0.85 (preferably at least 0.90), a mannuronate fraction ($F_M$) of no more than 0.15 (preferably no more than 0.10), and having at least 95% mole with a degree of polymerization less than 17 (preferably less than 14).

Further suitable alginate oligomers have a number average degree of polymerization in the range 5 to 18 (especially 7 to 15), a guluronate/galacturonate fraction ($F_G$) of at least 0.80 (preferably at least 0.85, especially at least 0.92), a mannuronate fraction ($F_M$) of no more than 0.20 (preferably no more than 0.15, especially no more than 0.08), and having at least 95% mole with a degree of polymerization less than 20 (preferably less than 17).

Further suitable alginate oligomers have a number average degree of polymerization in the range 5 to 18, a guluronate/galacturonate fraction ($F_G$) of at least 0.92, a mannuronate fraction ($F_M$) of no more than 0.08, and having at least 95% mole with a degree of polymerization less than 20.

Further suitable alginate oligomers have a number average degree of polymerization in the range 5 to 18 (preferably 7 to 15, more preferably 8 to 12, especially about 10), a guluronate/galacturonate fraction ($F_G$) of at least 0.80 (preferably at least 0.85, more preferably at least 0.90, especially at least 0.92, most especially at least 0.95), a mannuronate fraction ($F_M$) of no more than 0.20 (preferably no more than 0.15, more preferably no more than 0.10, especially no more than 0.08, most especially no more than 0.05), and having at least 95% mole with a degree of polymerization less than 20 (preferably less than 17, more preferably less than 14).

Further suitable alginate oligomers have a number average degree of polymerization in the range 7 to 15 (preferably 8 to 12), a guluronate/galacturonate fraction ($F_G$) of at least 0.92 (preferably at least 0.95), a mannuronate fraction ($F_M$) of no more than 0.08 (preferably no more than 0.05), and having at least 95% mole with a degree of polymerization less than 17 (preferably less than 14).

Further suitable alginate oligomers have a number average degree of polymerization in the range 5 to 18, a guluronate/galacturonate fraction ($F_G$) of at least 0.80, a mannuronate fraction ($F_M$) of no more than 0.20, and having at least 95% mole with a degree of polymerization less than 20.

Further suitable alginate oligomers have a number average degree of polymerization in the range 7 to 15, a guluronate/galacturonate fraction ($F_G$) of at least 0.85, a mannuronate fraction ($F_M$) of no more than 0.15, and having at least 95% mole with a degree of polymerization less than 17.

Further suitable alginate oligomers have a number average degree of polymerization in the range 7 to 15, a guluronate/galacturonate fraction ($F_G$) of at least 0.92, a mannuronate fraction ($F_M$) of no more than 0.08, and having at least 95% mole with a degree of polymerization less than 17.

Further suitable alginate oligomers have a number average degree of polymerization in the range 5 to 20, a guluronate fraction ($F_G$) of at least 0.85 and a mannuronate fraction ($F_M$) of no more than 0.15.

It will thus be seen that a particular class of alginate oligomers favoured according to the present invention is alginate oligomers defined as so-called "high G" or "G-block" oligomers i.e. having a high content of G residues or G-blocks (e.g. wherein at least 70% of the monomer residues are G, preferably arranged in G-blocks). However, other types of alginate oligomer may also be used, including in particular "high M" or "M-block" oligomers or MG-block oligomers, as described further below. Accordingly, it is alginate oligomers with high proportions of a single monomer type, and with said monomers of this type being present predominantly in contiguous sequences of that monomer type, that represent oligomers that are particularly preferred, e.g. oligomers wherein at least 70% of the monomer residues in the oligomer are G residues linked 1-4 to another G-residue, or more preferably at least 75%, and most preferably at least 80, 85, 90, 92, 93, 94, 95, 96, 97, 98, 99% of the monomers residues of the oligomer are G residues linked 1-4 to another G residue. This 1-4 linkage of two G residues can be alternatively expressed as a guluronic unit bound to an adjacent guluronic unit.

In a further embodiment at least, or more particularly more than, 50% of the monomer residues of the alginate oligomer may be M residues (i.e. mannuronate or mannuronic acid). In other words the alginate oligomer will contain at least or alternatively more than 50% mannuronate (or mannuronic acid) residues. Specific embodiments thus include alginate oligomers with (e.g. containing) 50 to 70% M (mannuronate) residues or e.g. 70 to 100% M (mannuronate) residues. Further specific embodiments also include oligomers containing 71 to 85% M residues or 85 to 100% M residues. Thus, a representative alginate oligomer for use according to this embodiment of the present invention will contain more than 70% M residues (i.e. more than 70% of the monomer residues of the alginate oligomer will be M residues).

In other embodiments at least 50% or 60%, more particularly at least 70% or 75%, even more particularly at least 80, 85, 90, 95 or 99% of the monomer residues are mannuronate. In one embodiment the alginate oligomer may be an oligomannuronate (i.e. a homooligomer of M, or 100% M).

In a further embodiment, the above described alginates of the invention have a primary structure wherein the majority of the M residues are in so called M-blocks. In this embodiment preferably at least 50%, more preferably at least 70 or 75%, and most preferably at least 80, 85, 90 or 95% of the M residues are in M-blocks. An M block is a contiguous sequence of at least two M residues, preferably at least 3 contiguous M residues, more preferably at least 4 or 5 contiguous M residues, most preferably at least 7 contiguous M residues.

In particular, at least 90% of the M residues are linked 1-4 to another M residue. More particularly at least 95%, more preferably at least 98%, and most preferably at least 99% of the M residues of the alginate are linked 1-4 to another M residue.

Other preferred oligomers are alginate oligomers wherein at least 70% of the monomer residues in the oligomer are M residues linked 1-4 to another M-residue, or more preferably at least 75%, and most preferably at least 80, 85, 90, 92, 93, 94, 95, 96, 97, 98, 99% of the monomers residues of the oligomer are M residues linked 1-4 to another M residue. This 1-4 linkage of two M residues can be alternatively expressed as a mannuronic unit bound to an adjacent mannuronic unit.

In a still further embodiment, the alginate oligomers of the invention comprise a sequence of alternating M and G residues. A sequence of at least three, preferably at least four, alternating M and G residues represents an MG block. Preferably the alginate oligomers of the invention comprise an MG block. Expressed more specifically, an MG block is a sequence of at least three contiguous residues consisting of G and M residues and wherein each non-terminal (internal) G residue in the contiguous sequence is linked 1-4 and 4-1 to an M residue and each non-terminal (internal) M residue in the contiguous sequence is linked 1-4 and 4-1 to a G residue. Preferably the MG block is at least 5 or 6 contiguous residues, more preferably at least 7 or 8 contiguous residues.

In a further embodiment the minority uronate in the alginate oligomer (i.e. mannuronate or guluronate) is found predominantly in MG blocks. In this embodiment preferably at least 50%, more preferably at least 70 or 75% and most preferably at least 80, 85, 90 or 95% of the minority uronate monomers in the MG block alginate oligomer are present in MG blocks. In another embodiment the alginate oligomer is arranged such that at least 50%, at least 60%, at least 70%, at least 80%, at least 85%, at least 90%, at least 95%, at least 99%, e.g. 100% of the G and M residues in the oligomer are arranged in MG blocks.

Although at its broadest, the invention extends to embodiments wherein at least 1% but less than 100% of the monomer residues of the oligomer are G residues (i.e. guluronate or guluronic acid), more particularly, and as defined further below, at least 30% of the monomer residues are G residues. Thus, at its broadest the MG block containing alginate oligomer may contain at least 1%, but less than 100%, guluronate (or guluronic acid) residues, but generally the MG block containing alginate oligomer will contain at least 30% (or at least 35, 40 or 45% or 50% G) but less than 100% G. Specific embodiments thus include MG block containing alginate oligomers with (e.g. containing) 1 to 30% G (guluronate) residues, 30 to 70% G (guluronate) residues or 70 to 99% G (guluronate) residues. Thus, a representative MG block containing alginate oligomer for use according to the present invention may contain more than 30%, but less than 70%, G residues (i.e. more than 30%, but less than 70%, of the monomer residues of the MG block alginate oligomer will be G residues).

Preferably more than 30%, more particularly more than 35% or 40%, even more particularly more than 45, 50, 55, 60 or 65%, but in each case less than 70%, of the monomer residues of the MG block containing alginate oligomer are guluronate. Alternatively, less than 70%, more preferably less than 65% or 60%, even more preferably less than 55, 50, 45, 40 or 35%, but in each case more than 30% of the monomer residues of the MG block containing alginate oligomer are guluronate. Any range formed by any combination of these values may be chosen. Therefore for instance the MG block containing alginate oligomer can have e.g. between 35% and 65%, 40% and 60% or 45% and 55% G residues.

In another embodiment the MG block containing alginate oligomer may have approximately equal amounts of G and M residues (e.g. ratios between 65% G/35% M and 35% G/65% M, for instance 60% G/40% M and 40% G/60% M; 55% G/45% M and 45% G/55% M; 53% G/47% M and 47% G/53% M; 51% G/49% M and 49% G/51% M; e.g. about 50% G and about 50% M) and these residues are arranged predominantly, preferably entirely or as completely as possible, in an alternating MG pattern (e.g. at least 50% or at least 60, 70, 80, 85, 90 or 95% or 100% of the M and G residues are in an alternating MG sequence).

The level, or amount, of anticoagulation achieved may vary depending up on the precise circumstances, e.g. the manner and context in which the alginate oligomers are used, the conditions under which they are used and the composition of the alginate oligomer. As shown in the Examples, alginate oligomers of varying sizes, G and M content and monomer arrangement display varying levels of anticoagulation effect. The invention therefore provides the skilled man with the means to select, in accordance with the invention, an alginate oligomer of a structure which has anticoagulation properties (e.g. potency and duration of effect) that best, or better, meets his needs in the context in which he is working, e.g. the clotting characteristics of the patient or blood sample of interest. Thus, the availability of different alginate oligomers which may have different anticoagulant effects in a given system of interest opens up the possibility of tailoring the properties of the alginate oligomer anticoagulant to the system in question. Combinations of alginate oligomers of different sizes, G and M content and monomer arrangement may be used together to create an even more precisely tailored anticoagulation effect. In other embodiments an alginate oligomer of the invention may have distinct regions of monomer content and structure that together contribute to an overall tailored anticoagulation effect. Of course, the oligomer structure, or parts thereof, may be further selected to facilitate formulation and/or immobilisation onto or into materials and surfaces.

In certain embodiments the terminal uronic acid residues of the oligomers of the invention do not have a double bond, especially a double bond situated between the $C_4$ and $C_5$ atom. Such oligomers may be described as having saturated terminal uronic acid residues. Thus, in other embodiments the alginate oligomers of the invention have unsaturated terminal uronic acid residues. The skilled man would be able to prepare oligomers with saturated terminal uronic acid residues without undue burden. This may be through the use of production techniques which yield such oligomers, or by converting (saturating) oligomers produced by processes that yield oligomers with unsaturated terminal uronic acid residues.

The alginate oligomer will typically carry a charge and so counter ions for the alginate oligomer may be any physiologically tolerable ion, especially those commonly used for charged drug substances, e.g. sodium, potassium, ammonium, chloride, mesylate, meglumine, etc. Ions which promote alginate gelation e.g. group 2 metal ions may also be used.

While the alginate oligomer may be a synthetic material generated from the polymerisation of appropriate numbers of guluronate and mannuronate residues, the alginate oligomers of use in the invention may conveniently be obtained, produced or derived from natural sources such as those mentioned above, namely natural alginate source materials.

Polysaccharide to oligosaccharide cleavage to produce the alginate oligomer useable according to the present invention may be performed using conventional polysaccharide lysis techniques such as enzymatic digestion and acid hydrolysis. In one favoured embodiment acid hydrolysis is used to prepare the alginate oligomers on the invention. In other embodiments enzymic digestion is used with an additional processing step(s) to saturate the terminal uronic acids in the oligomers.

Oligomers may then be separated from the polysaccharide breakdown products chromatographically using an ion exchange resin or by fractionated precipitation or solubilisation or filtration. U.S. Pat. No. 6,121,441 and WO 2008/125828, which are explicitly incorporated by reference herein in their entirety, describe a process suitable for preparing the alginate oligomers of use in the invention. Further information and discussion can be found in for example in "Handbooks of Hydrocolloids", Ed. Phillips and Williams, CRC, Boca Raton, Fla., USA, 2000, which textbook is explicitly incorporated by reference herein in its entirety.

The alginate oligomers may also be chemically modified, including but not limited to modification to add charged groups (such as carboxylated or carboxymethylated glycans) and alginate oligomers modified to alter flexibility (e.g. by periodate oxidation).

Alginate oligomers (for example oligoguluronic acids) suitable for use according to the invention may conveniently be produced by acid hydrolysis of alginic acid from, but not limited to, *Laminaria hyperbora* and *Lessonia nigrescens*, dissolution at neutral pH, addition of mineral acid reduce the pH to 3.4 to precipitate the alginate oligomer (oligoguluronic acid), washing with weak acid, resuspension at neutral pH and freeze drying.

The alginates for production of alginate oligomers of the invention can also be obtained directly from suitable bacterial sources e.g. *Pseudomonas aeruginosa* or *Azotobacter vinelandii*.

In embodiments where alginate oligomers which have primary structures in which the majority of the G residues are arranged in G-blocks rather than as single residues are required, algal sources are expected to be most suitable on account of the fact that the alginates produced in these organisms tend to have these structures. The bacterial sources may be more suitable for obtaining alginate oligomers of different structures.

The molecular apparatus involved in alginate biosynthesis in *Pseudomonas fluorescens* and *Azotobacter vinelandii* has been cloned and characterised (WO 94/09124; Ertesvåg, H., et al, Metabolic Engineering, 1999, Vol 1, 262-269; WO 2004/011628; Gimmestad, M., et al (supra); Remminghorst and Rehm, Biotechnology Letters, 2006, Vol 28, 1701-1712; Gimmestad, M. et al, Journal of Bacteriology, 2006, Vol 188(15), 5551-5560) and alginates of tailored primary structures can be readily obtained by manipulating these systems.

The G content of alginates (for example an algal source material) can be increased by epimerisation, for example with mannuronan C-5 epimerases from *A. vinelandii* or other epimerase enzymes. Thus, for example in vitro epimerisation may be carried out with isolated epimerases from *Pseudomonas* or *Azotobacter*, e.g. AlgG from *Pseudomonas fluorescens* or *Azotobacter vinelandii* or the AlgE enzymes (AlgE1 to AlgE7) from *Azotobacter vinelandii*. The use of epimerases from other organisms that have the capability of producing alginate, particularly algae, is also specifically contemplated. The in vitro epimerisation of low G alginates with *Azotobacter vinelandii* AlgE epimerases is described in detail in Ertesvåg et al (supra) and Strugala et al (Gums and Stabilisers for the Food Industry, 2004, 12, The Royal Society of Chemistry, 84-94).

To obtain G-block containing alginates or alginate oligomers, epimerisation with one or more *Azotobacter vinelandii* AlgE epimerases other than AlgE4 is preferred as these enzymes are capable of producing G block structures. On the other hand AlgE4 epimerase can be used to create alginates or alginate oligomers with alternating stretches of M/G sequence or primary structures containing single G residue as it has been found that this enzyme seems preferentially to epimerise individual M residues so as to produce single G residues linked to M residues rather than producing G blocks. Particular primary structures can be obtained by using different combinations of these enzymes.

Mutated versions of these enzymes or homologues from other organisms are also specifically contemplated as of use. WO 94/09124 describes recombinant or modified mannuronan C-5 epimerase enzymes (AlgE enzymes) for example encoded by epimerase sequences in which the DNA sequences encoding the different domains or modules of the epimerases have been shuffled or deleted and recombined. Alternatively, mutants of naturally occurring epimerase enzymes, (AlgG or AlgE) may be used, obtained for example by site directed or random mutagenesis of the AlgG or AlgE genes.

A different approach is to create *Pseudomonas* and *Azotobacter* organisms that are mutated in some or all of their epimerase genes in such a way that those mutants produce alginates of the required structure for subsequent alginate oligomer production, or even alginate oligomers of the required structure and size (or molecular weight). The generation of a number of *Pseudomonas fluorescens* organisms with mutated AlgG genes is described in detail in WO 2004/011628 and Gimmestad, M., et al, 2003 (supra). The generation of a number of *Azotobacter vinelandii* organisms with mutated AlgE genes is disclosed in Gimmestad, M., et al, 2006 (supra). The skilled man would be able to use this teaching to produce new mutants that could be used to give rise to the alginate oligomers of the invention without undue burden.

A further approach is to delete or inactivate the endogenous epimerase genes from an *Azotobacter* or a *Pseudomonas* organism and then to introduce one or more exogenous epimerase genes, which may or may not be mutated (i.e. may be wild-type or modified) and the expression of which may be controlled, for example by the use of inducible or other "controllable promoters". By selecting appropriate combinations of genes, alginates of predetermined primary structure can be produced.

A still further approach would be to introduce some or all of the alginate biosynthesis machinery of *Pseudomonas* and/or *Azotobacter* into a non-alginate producing organism (e.g. *E. coli*) and to induce the production of alginate from these genetically modified organisms.

When these culture-based systems are used, the primary structure of the alginate or alginate oligomer products can be influenced by the culture conditions. It is well within the capabilities of the skilled man to adjust culture parameters such as temperature, osmolarity, nutrient levels/sources and atmospheric parameters in order to manipulate the primary structure of the alginates produced by a particular organism.

References to "G residues/G" and "M residues/M" or to guluronic acid or mannuronic acid, or guluronate or mannuronate are to be read interchangeably as references to guluronic acid/guluronate and mannuronic acid/mannuronate (specifically α-L-guluronic acid/guluronate and β-D-mannuronic acid/mannuronate), and further include derivatives thereof in which one or more available side chains or groups have been modified without resulting in a capacity to inhibit or prevent blood coagulation that is substantially lower than that of the unmodified oligomer. Common saccharide modifying groups would include acetyl, sulphate, amino, deoxy, alcohol, aldehyde, ketone, ester and anhydro groups. Any of these groups, except for sulphate, may be used to modify the alginate oligomers according to the present invention; it is a feature of the alginate oligomers according to the present invention that they do not carry a sulphate group. The alginate oligomers may also be chemically modified to add charged groups (such as carboxylated or carboxymethylated glycans), and to alter flexibility (e.g. by periodate oxidation). The skilled man would be aware of still further chemical modifications that can be made to the monosaccharide subunits of oligosaccharides and these can be applied to the alginate oligomers of the invention.

The invention encompasses the use of a single alginate oligomer or a mixture (multiplicity/plurality) of different alginate oligomers. Thus, for example, a combination of different alginate oligomers (e.g. two or more) may be used. In this regard, as mentioned above, a combination of alginate oligomers may be selected that together give an advantageous profile of anticoagulation properties. This may be a combination of different oligomer sizes, different G and M contents and/or different monomer arrangements.

By "blood coagulation" it is meant the natural process by which an insoluble matrix of fibrin filaments is formed from fluid blood. This includes both the tissue factor pathway and the contact pathway described above. In accordance with the invention "blood coagulation" extends to the process that may be observed in plasma (i.e. a product obtained from the removal of blood cells from whole blood and which retains all of the clotting factors). Similarly the term extends to the process that is observed in artificial mixtures comprising blood clotting factors that are sufficiently complete to be able to form fibrin clots under conducive conditions.

"Blood plasma" refers to the liquid component of whole blood. This solution contains numerous proteins and other macromolecules, electrolytes and sugars. In particular it contains all of the blood clotting factors involved in blood coagulation.

In accordance with the invention the term "composition comprising blood plasma" includes not only whole blood or blood from which one or more blood cell type, e.g. erythrocytes or leukocytes, have been removed, but also compositions of substantially equivalent chemical makeup to plasma and compositions comprising blood clotting factors that are sufficiently complete to form fibrin clots under conducive conditions (e.g. compositions comprising Factors XII, XI, X, IX, VIII, V, prothrombin and fibrinogen and optionally Factor XIII, or compositions comprising Factors VII, III, X, V, prothrombin and fibrinogen and optionally Factor XIII). Functionally equivalent derivatives and homologs may be incorporated. In certain embodiments these compositions may not be derived, or may be only partially derived, from whole blood. The composition comprising blood plasma can be plasma in which some or all platelets have been retained.

The term "blood-derived product" is accordingly to be interpreted in an analogous way to refer to any product that is or can be derived from blood, and includes in particular fractions of blood or blood products, and in particular such fractions or products which retain the ability or capacity to form clots (i.e. to coagulate). A blood-derived product may therefore include any product which contains clotting factors sufficient to form a clot, including blood plasma or any equivalent product or fraction.

Preferably the composition is a liquid composition. Preferably the composition is a sterile composition. Preferably the blood plasma is human blood plasma or the clotting factors present in the composition comprising blood plasma are human, however functionally equivalent non-human homologs may be present. Preferably the composition comprising blood plasma is whole blood or a composition comprising whole blood. In certain embodiments the whole blood may or may not contain proteins heterologous to the host organism. Preferably the whole blood has been freshly collected, e.g. less than 10, 9, 8, 7, 6, 5, 4, 3, 2 or 1 minutes prior to contact with the alginate oligomer. In other embodiments the composition is not fully coagulated, e.g. is partially coagulated or preferably substantially uncoagulated.

"Prevention or inhibition of blood coagulation" is used broadly herein to encompass both absolute prevention of blood coagulation and any negative effect on the onset of blood coagulation or on a pre-existing clot or the number of clots in the composition comprising blood plasma (e.g. the circulating blood or the circulatory system of a subject). For instance this may be a delay in the initiation of the coagulation process or a slowing in one or more steps of the process or the process as a whole. This may also be seen in a reduction in the size and/or density of a clot, or a reduction in the rate at which a pre-existing or growing clot increases in size and/or density. It may further be seen in a reduction in the physical integrity, or any sort of structural deterioration, of a pre-existing or growing clot, although in certain embodiments the term does not encompass thrombolysis of, or a thrombolytic effect on, an established or pre-existing clot. It may further be seen in a reduction in the number of clots in the composition comprising blood plasma (e.g. the circulating blood or the circulatory system of a subject), or a reduction in the rate at which the number of clots are growing. It may also be viewed as a reduction in the capacity of a clot to be detrimental to the health or well-being of a subject. "Anticoagulation" as used herein should be interpreted consistent with the foregoing. It will be seen that these surprising effects of alginate oligomers as defined herein can therefore be used to regulate or control blood coagulation.

Any delay in the coagulation (e.g. a reduction in the rate of coagulation) and/or reduction of extent of coagulation may be taken as an indication of anticoagulant activity or effect according to the invention. Thus, for example, an anticoagulant effect may be manifest as a reduction of at least 10, 15, 20, 25 or 30% in coagulation, as compared to the coagulation seen in the absence of the alginate oligomer.

The extent of coagulation of blood or of a composition containing blood plasma may readily be determined in simple in vitro tests, for example as described in the Examples below. Thus the time taken for coagulation of a blood sample to occur may be used as a measure of anticoagulant effect, and an increased coagulation time in the presence of alginate oligomer compared to a control (e.g. the coagulation time in the absence of the alginate oligomer, e.g. an untreated control, or of a positive control substance) may be indicative of an anticoagulant effect.

Alternatively, a determination of anticoagulant effect may be made by other means, for example by comparing the extent and/or rate of clot formation in the presence and absence of alginate oligomer, for example the size and/or number of clots formed, or the size and/or number of clots formed per unit of time. By way of example, this may be in a test system, for example determining the extent or rate of clot formation on or at an artificial surface in contact with blood or with a composition comprising blood plasma in the presence or absence of alginate oligomer. A decrease in the extent and/or rate of clot formation in the presence of alginate oligomer as compared to the absence of alginate oligomer may be taken as indicative of an anticoagulant effect.

The physical properties of a blood clot may be measured by any convenient means, e.g. ultrasound, angiography, CT, or simple visual measurement. In other embodiments coagulation, and therefore its inhibition or prevention, may be measured by a routine coagulation test (or blood clotting test) conveniently using a blood coagulometer, e.g. thromboelastography, the thrombin generation test, the thrombodynamics test, the partial thromboplastin time (PTT) (or activated partial thromboplastin time (aPTT or APTT)) test or the prothrombin time test. In preferred embodiments the methods of the invention will result in a clinically relevant reduction in the capacity of a subject's blood to coagulate or the rate at which a subject's blood coagulates. In alternative embodiments the procedure outlined in the Examples may be used to measure coagulation time and in which case the methods of the invention will result in a clinically relevant increase in coagulation time for the blood of a subject.

"Treatment" when used in relation to the treatment of a medical disease or condition associated with blood coagulation in accordance with the invention is used broadly herein to include any therapeutic effect, i.e. any beneficial effect on the disease or condition. Thus, not only included is eradication or elimination of the disease or condition, or cure of the subject of the disease or condition, but also an improvement in the disease or condition or overall well-being of the subject. Thus included, for example, is an improvement in any symptom or sign of the disease or condition, or in any clinically accepted indicator of the disease or condition (for example, a lowering in the number of circulating blood clots or an increase oxygenation downstream of a thrombosis). In the presently claimed treatments it may be that pre-existing blood clots are not fully eradicated or the formation of new clots is not completely halted, but the treatments are sufficient to inhibit these processes to such an extent that the target disease or condition is fully resolved, or at least resolved to some extent, preferably to an extent acceptable to the subject. Treatment thus includes both curative and palliative therapy, e.g. of a pre-existing or diagnosed disease or condition, i.e. a reactionary treatment.

"Prevention" when used in relation to the treatment of a medical disease or condition associated with blood coagulation in accordance with the invention is used broadly herein to include any prophylactic or preventative effect. It thus includes delaying, limiting, reducing or preventing the disease or condition or the onset of the disease or condition, or one or more symptoms or indications thereof, for example relative to the condition or symptom or indication prior to the prophylactic treatment. Prophylaxis thus explicitly includes both absolute prevention of occurrence or development of the disease or condition, or symptom or indication thereof, and any delay in the onset or development of the condition or symptom or indication, or reduction or limitation of the development or progression of the condition or symptom or indication.

In accordance with the invention "anticoagulation therapy" and "antithrombotic (or antithrombosis) therapy" include both preventative treatment and therapeutic treatment of an existing or ongoing condition and so these terms should be interpreted consistent with the foregoing.

Viewed more particularly, in the methods of the invention, the composition comprising plasma will be contacted with an effective amount of the alginate oligomer, more particularly an amount of the alginate oligomer that provides measurable inhibition or prevention of blood coagulation. A pharmaceutically effective amount of the alginate oligomer is that amount of alginate oligomer that provides a measurable treatment or prevention of a disease or condition associated with blood coagulation. The skilled man would easily be able to determine what an effective/pharmaceutically effective amount of alginate oligomer would be on the basis of routine dose response protocols and, conveniently, the routine techniques for assessing blood coagulation described above. The skilled man would, without undue burden, also be able to optimise these amounts and be able to ensure safe use of the alginate oligomers of the invention.

In a therapeutic context, suitable doses of alginate oligomer will vary from subject to subject and can be determined by the physician or veterinary practitioner in accordance with the weight, age and sex of the subject, the severity of the condition, the mode of administration and also the particular alginate oligomer selected, e.g. based on its size, G and M content and/or monomer arrangement. Typically the alginate oligomers of the invention will be applied to the location undergoing treatment at a local concentration of at least 0.05%, preferably at least 0.1%, 0.2%, 0.5%, 1%, 2%, 3% 4% or at least 5%, more preferably at least 6% and most preferably at least 10% weight by volume.

Diseases and conditions associated with blood coagulation, more specifically unwanted or inappropriate blood coagulation, include but are not limited to venous thrombosis (e.g. deep vein, portal vein, renal vein, jugular vein and cerebral venous sinus thrombosis), arterial thrombosis (e.g. coronary, carotid and hepatic artery thrombosis), atherosclerosis, vein graft failure, arterial graft failure, stroke, cardiac infarction, pulmonary embolism, and thrombophilia (also referred to as hypercoagulability or prothrombotic state). The alginate oligomers of the invention may be used to treat or prevent any and all of these diseases and conditions. Treatment may involve systemic or local administration of the alginate oligomers.

A further major clinical problem associated with blood coagulation relates to the induction of thromboses by in-dwelling and implantable medical, surgical or prosthetic devices. Exposure of blood and/or interstitial fluid to the artificial, i.e. abiotic (e.g. plastic, rubber, silicone, metal or glass), surfaces of such products promotes the formation of thromboses. It has also been reported that tissue transplants can give rise to these thromboses and may cause problems at the site of the transplanted tissue or remote parts of the circulatory system should those thromboses embolise.

The alginate oligomers of the invention can therefore be used to inhibit or prevent the formation of thromboses on such devices or transplant tissues. This may include any kind of line, including catheters (e.g. central venous and peripheral venous catheters), heart valves, vascular stents, artificial joints, intrauterine devices, pacemakers, tracheostomy tubes, radiotherapy wires and soft tissue implants. Such devices include devices which, when in use may be partly in-dwelling. Transplant tissue may include heart (e.g. heart valve), lung, kidney, liver, pancreas, intestine and corneal tissue, arterial and venous grafts and skin.

Such treatments may comprise the local or systemic administration of alginate oligomers to a subject in which an implantable device or a tissue transplant has been or will be implanted. In other embodiments the implantable/in-dwelling device or tissue transplant may be implanted after being provided with (receiving a treatment with), e.g. a coating of, an alginate oligomer of the invention on surfaces that may come into contact with blood. Such treatments may be applied to the implantable surfaces just prior to, or substantially contemporaneously with, implantation, e.g. by spraying the relevant surfaces of the implantable device or the tissue transplant with a liquid formulation comprising the alginate oligomer. In other embodiments the implantable or in-dwelling surface(s) of the devices may contain or carry, e.g. may incorporate, or may be impregnated or coated with, an alginate oligomer according to the invention. In these embodiments alginate oligomers may be coated onto the implantable/in-dwelling surfaces or provided as part of a surface coating. This may occur before, during or after formation of the implantable surface and immobilisation may be effected through covalent or non-covalent interactions, e.g. ionic or electrostatic interactions. By way of representative example, alginate oligomers of suitable monomer composition may be provided on a surface as a, or part of a, cation-induced gel. In still further embodiments the alginate oligomer may be provided or included in a haemo-compatible coating comprising one or more further haemo-compatible compounds, e.g. heparin, heparan sulphate, hyaluronan, polyethylene glycol or dextran, or indeed any other bioactive agent having anticoagulant activity, or a compound or agent having a passive haemocompatible property, e.g. a haemocompatible polymer or plastic.

A further major clinical problem associated with blood coagulation relates to the induction of thromboses during surgical procedures. Incisions into the tissues of a subject can become loci for thromboses which in turn may embolise and travel to another part of the circulatory system at which they lodge and give rise to the diseases and conditions discussed above.

The alginate oligomers of the invention can therefore be used before, during and/or after surgical procedures to inhibit or prevent the formation of thromboses at sites of surgical incision. Such treatments may comprises the systemic or, more conveniently, the local administration of alginate oligomers to a subject undergoing, about to undergo or recovering from a surgical procedure.

Specifically, the alginate oligomers of the invention can be taken as a prophylactic treatment, for example to prevent, or at least minimise the risk, of thrombotic disease (e.g. those described above). Generally, subjects in need of treatment or prophylaxis according to the invention will be diagnosed as suffering with or at risk from a disease or condition associated with blood coagulation, e.g. those discussed above. Such subjects include, but are not limited to, subjects that will be or are immobile for prolonged periods, subjects with arterial fibrillation, subjects with atherosclerotic plaques, subjects with or receiving implantable medical, surgical or prosthetic devices, subjects undergoing, about to undergo or recovering from a surgical procedure, subjects with congenital thrombophilia (e.g. factor V Leiden, prothrombin G20210A, antithrombin III deficiency, protein C deficiency, protein S deficiency, factor XIII mutation, familial dysfibrinogenemia), and subjects with acquired thrombophilia (e.g. those with antiphospholipid syndrome, heparin-induced thrombocytopenia (HIT), nocturnal hemoglobinuria (PNH), haematological conditions associated with sluggish blood (for example, sickle-cell disease, polycythemia vera and essential thrombocytosis (excess platelets)), cancer (particularly metastatic tumours), nephrotic syndrome, inflammatory bowel disease (ulcerative colitis and Crohn's disease)), obesity and subjects that are pregnant.

The subject may be any human or non-human vertebrate subject, but more particularly may be a vertebrate, e.g. a vertebrate selected from mammals, birds, amphibians, fish and reptiles. The non-human vertebrate may be a livestock or a domestic animal or an animal of commercial value, including laboratory animals or an animal in a zoo or game park. Representative animals therefore include dogs, cats, rabbits, mice, guinea pigs, hamsters, horses, pigs, sheep, goats, cows, chickens, turkeys, guinea fowl, ducks, geese, parrots, budgerigars, pigeons, salmon, trout, cod, haddock, sea bass and carp. Veterinary uses of the invention are thus covered. The subject may be viewed as a patient. Preferably the subject is a human.

In certain embodiments the subject does not have an infection, e.g. a bacterial, fungal, protozoal, algal or parasite infection, displaying pathological indicators. More particularly in certain such embodiments the subject does not have a biofilm infection. In other embodiments the subject does not have hyperviscous mucus or is need of reduction in mucus viscosity.

In one embodiment of the invention the alginate oligomers may be used in the methods or uses of the invention in conjunction or combination with a further blood anti-coagulant (hereinafter "further anticoagulant")

In the context of a therapeutic use, such an anti-microbial agent may be any clinically-useful anticoagulant, e.g. the vitamin K antagonists (e.g. warfarin, acenocoumarol, phenprocoumon, atromentin and phenindione), heparin, low molecular weight heparin, synthetic pentasaccharide inhibitors of factor Xa (e.g. fondaparinux and idraparinux, direct factor Xa inhibitors (e.g. rivaroxaban and apixaban), direct thrombin inhibitors (e.g. hirudin, lepirudin, bivalirudin, argatroban, dabigatran, ximelagatran, antithrombin protein, batroxobin and hementin).

In a further embodiment of the invention the alginate oligomer may be used in the methods or uses of the invention in conjunction or combination with a thrombolytic agent. Thrombolytic agents digest or break down pre-existing blood clots and include tissue plasminogen activator (t-PA), alteplase, reteplase, tenecteplase, anistreplase, streptokinase and urokinase.

In one still further embodiment of the invention the alginate oligomers may be used in the methods of the invention in conjunction or combination with an antiplatelet agent. Antiplatelet agents inhibit platelet aggregation and include the irreversible cyclooxygenase inhibitors (e.g. aspirin), adenosine diphosphate (ADP) receptor inhibitors (e.g. clopidogrel, prasugrel, ticagrelor, ticlopidine, phosphodiesterase inhibitors (e.g. cilostazol), glycoprotein IIB/IIIA inhibitors (e.g. abciximab, eptifibatide, tirofiban) adenosine reuptake inhibitors (e.g. dipyridamole), thromboxane inhibitors (e.g. terutroban)

The alginate oligomers proposed for use according to the invention and the further anticoagulant, thrombolytic agent or antiplatelet agent, may for example be administered together, in a single pharmaceutical formulation or composition, or separately (i.e. separate, sequential or simultaneous administration). Thus, the alginate oligomers of the invention and the further anticoagulant, thrombolytic agent or antiplatelet agent may be combined, e.g. in a pharmaceutical kit or as a combined ("combination") product.

The invention therefore also provides products (e.g. a pharmaceutical kit or a combined ("combination") product) or compositions (e.g. a pharmaceutical composition) wherein the product or composition comprises an alginate oligomer as herein defined and a further anticoagulant, thrombolytic agent and/or antiplatelet agent. Such pharmaceutical products and pharmaceutical compositions are preferably adapted for use in the medical methods of the invention.

The use of alginate oligomers as herein defined to manufacture such pharmaceutical products and pharmaceutical compositions for use in the medical methods of the invention is also contemplated.

The alginate oligomers of the invention may be administered to the subject in any convenient form or by any convenient means, e.g. by topical, oral, parenteral, enteral, parenteral routes or by inhalation. Preferably the alginate will be administered by topical, oral or parenteral routes or by inhalation. That alginate oligomers may be administered via many different routes is an advantage over currently available anticoagulants.

The skilled man will be able to formulate the alginate oligomers of the invention into pharmaceutical compositions that are adapted for these routes of administration according to any of the conventional methods known in the art and widely described in the literature.

The present invention therefore also provides a pharmaceutical composition for use in any of the above-mentioned methods or uses comprising an alginate oligomer as defined herein together with at least one pharmaceutically acceptable carrier, diluent or excipient. This composition may also comprise other therapeutic agents as described above.

More specifically, the alginate oligomers of the invention may be incorporated, optionally together with other active agents, with one or more conventional carriers, diluents and/or excipients, to produce conventional galenic preparations such as tablets, pills, powders (e.g. inhalable powders), lozenges, sachets, cachets, elixirs, suspensions, emulsions, solutions, syrups, aerosols (as a solid or in a liquid medium), sprays (e.g. nasal sprays), compositions for use in nebulisers, ointments, soft and hard gelatine capsules, suppositories, pessaries, sterile injectable solutions, sterile packaged powders, and the like. Sterile inhalable and sterile injectable compositions are of particular note.

Examples of suitable carriers, excipients, and diluents are lactose, dextrose, sucrose, sorbitol, mannitol, starches, gum acacia, calcium phosphate, inert alginate polymers, tragacanth, gelatine, calcium silicate, microcrystalline cellulose, polyvinylpyrrolidone, cellulose, water syrup, water, water/ethanol, water/glycol, water/polyethylene, hypertonic salt water, glycol, propylene glycol, methyl cellulose, methylhydroxybenzoates, propyl hydroxybenzoates, talc, magnesium stearate, mineral oil or fatty substances such as hard fat or suitable mixtures thereof. Excipients and diluents of note are mannitol and hypertonic salt water (saline).

The compositions may additionally include lubricating agents, wetting agents, emulsifying agents, suspending agents, preserving agents, sweetening agents, flavouring agents, and the like. Additional therapeutically active agents may be included in the pharmaceutical compositions, as discussed above in relation to combination therapies above.

Parenterally administrable forms, e.g., intravenous solutions, should be sterile and free from physiologically unacceptable agents, and should have low osmolarity to minimize irritation or other adverse effects upon administration and thus solutions should preferably be isotonic or slightly hypertonic, e.g. hypertonic salt water (saline). Suitable vehicles include aqueous vehicles customarily used for administering parenteral solutions such as sterile water for injection, Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405-1412 and 1461-1487 (1975) and The National Formulary XIV, 14th ed. Washington: American Pharmaceutical Association (1975). The solutions can contain preservatives, antimicrobial agents, buffers and antioxidants conventionally used for parenteral solutions, excipients and other additives which are compatible with the biopolymers and which will not interfere with the manufacture, storage or use of products.

For topical administration the alginate oligomer can be incorporated into creams, ointments, gels, transdermal patches and the like. Simple sterile solutions of alginate oligomer or simple sterile liquid compositions comprising alginate oligomer may be especially convenient for use during surgical procedures and for treating implantable devices. The alginate oligomers can also be incorporated into medical dressings, for example wound dressings e.g. woven (e.g. fabric) dressings or non-woven dressings (e.g. gels or dressings with a gel component). The use of alginate polymers in dressings is known, and such dressings, or indeed any dressings, may further incorporate the alginate oligomers of the invention.

Further topical systems that are envisaged to be suitable are in situ drug delivery systems, for example gels where solid, semi-solid, amorphous or liquid crystalline gel matrices are formed in situ and which may comprise the alginate oligomer (which may be any alginate oligomer as herein defined). Such matrices can conveniently be designed to control the release of the alginate oligomer from the matrix, e.g. release can be delayed and/or sustained over a chosen period of time. Such systems may form gels only upon contact with biological tissues or fluids. Typically the gels are bioadhesive. Delivery to any body site that can retain or be adapted to retain the pre-gel composition can be targeted by such a delivery technique. Such systems are described in WO 2005/023176.

The relative content of the alginate oligomer in the compositions of the invention can vary depending on the dosage required and the dosage regime being followed and this will depend on the subject to be treated and the location and identity of the thrombus or the likely site(s) of formation. Preferably, the composition will comprise an amount of alginate oligomer the will provide measurable inhibition or prevention of blood coagulation and/or measurable, preferably clinically relevant, prevention or treatment of the target disease or condition associated with blood coagulation.

Preferably the composition or product will comprise sufficient alginate oligomer that upon administration to a subject or application to a location, the local concentration at the target location of the oligomer will be at least 0.05%, preferably at least 0.1%, 0.2%, 0.5%, 1%, 2%, 3%, 4%, 5%, 6%, 7% or 8% and most preferably at least 10% (weight by volume). The skilled man would know that the amounts of alginate can be reduced if a multiple dosing regime is followed or increased to minimise the number of administrations or applications.

The compositions and products of the invention will typically comprise 1% to 99%, 5% to 95%, 10% to 90% or 25% to 75% alginate oligomer, allowance being made for other ingredients.

The methods of the invention also find application in in vitro and ex vivo contexts. Blood and blood derived products, including plasma, are commonly used in numerous medical procedures. For instance blood and plasma transfusions are common place during surgical procedures and trauma therapy. Collection of such products from donors is more often than not removed both physically and temporarily from administration to the patient. Accordingly, such products must be handled in vitro at some stage of their useful life. Blood products derived from blood must by definition undergo a certain amount of in vitro processing.

In addition, blood is routinely extracted from patients in order for in vitro diagnostic and prognostic tests to be performed thereon.

In these areas it is imperative that coagulation of the blood/blood product does not occur and it is standard practice for anticoagulants such as EDTA, citrate and oxalate to be added to the blood upon collection or shortly thereafter to ensure coagulation is retarded. If that blood undergoes processing of any kind the presence of an anticoagulant will be maintained to ensure coagulation does not occur at a later time.

Thus the alginate oligomers of the present invention may be used to inhibit or prevent coagulation in in vitro compositions comprising blood plasma, preferably whole blood. The low toxicity of alginate oligomers make them especially advantageous in this context as such treated compositions may be administered to patients without the anticoagulant causing toxicity. Preferably the alginate oligomer in contacted with the composition comprising blood plasma (e.g. whole blood) substantially upon collection, e.g. within 10, 9, 8, 7, 6, 5, 4, 3, 2 or 1 minutes of collection, preferably contemporaneously. In other embodiments the alginate oligomer is contacted with the composition comprising blood plasma, e.g. whole blood, during storage. This contacting may occur a plurality of times over the life of the composition.

The alginate oligomer may accordingly be added to the composition comprising blood plasma. Alternatively or additionally it may be added to or provided in a vessel to which the composition is to be introduced, or in which it is to be contained e.g. blood collection tubes, storage bags etc. Indeed, any material (e.g. vessel or conduit (line) or surface or device) with which the plasma-containing composition may come into contact (e.g. test equipment as well as collection or storage equipment, medical or surgical devices or equipment, implantable medical devices etc.) may be provided with the alginate oligomer. Thus, any material which is intended to, or likely to, come into contact with a composition comprising blood plasma may be contacted with an alginate oligomer as defined herein according to the uses and methods of the present invention.

Representative products and devices include diagnostic and research testing products and devices, including for example sensors and other devices for testing blood or blood components, and products, including consumables, for use therewith e.g. testing strips or sticks, plates, vials or vessels etc.

In embodiments where the composition is or has been derived from whole blood and is to be administered to a patient in due course, that composition may be considered to be ex vivo. In other words the methods of the invention as set out above are in certain embodiments not practiced or carried out in or on the human or animal body (e.g. wherein the step of using the alginate oligomer does not occur in or on the human or animal body). In the context of this invention any method that is not a method practiced on or in the body of a human or an animal (e.g. by therapy or surgery) may be viewed as an in vitro method, which may include ex vivo methods. Nevertheless as is clear from the forgoing, such in vitro/ex vivo methods may still be performed with a clinical application in mind.

One particular example that illustrates this would be blood dialysis. Anticoagulants are often used during blood dialysis to ensure that problematic thrombi do not form within the dialysis machinery and transfer to the patient with the dialysed blood. Administration of the anticoagulant to the patient would amount to an in vivo treatment. On the other hand, administration of the anticoagulant to the blood while it is outside of the patient and within the dialysis equipment and conduits would amount to an ex vivo/in vitro treatment.

By analogy to dialysis, the alginate oligomers as defined herein may also be used as anticoagulants according to the present invention in any method of, or involving plasmapheresis, that is where blood is removed from the body, plasma or one or more plasma components are removed or treated, and the blood cells and/or plasma are returned to the body. More generally the use of alginate oligomers according to the present invention may be applicable to any extracorporeal method of blood treatment.

In view of the commonly felt need to maintain in vitro blood and blood products in sterile conditions it is routine to supply the sterile collection vessels and conduits with an anticoagulant already present therein at an effective amount. The alginate oligomers may be used according to the invention in the same way.

Thus the invention provides sterile blood collection vessels and conduits containing an alginate oligomer as defined herein. The alginate oligomer may be provided in any convenient form, e.g. free (e.g. as part of a solution or as a solid, e.g. lyophilised solid) or in immobilised form, e.g. as a pretreatment (e.g. coating) on the internal surfaces of the vessels and conduits. Blood collection vessels include but are not limited to blood transfusion bags, test tubes or vials (preferably vacuum), and syringes.

The invention further provides dialysis or plasmapheresis consumables, equipment and machinery, including disposable conduits receptacles and filters which contain or which have surfaces that have been pretreated, e.g. coated, with an alginate oligomer as defined herein.

By "pretreated" it is meant that the surface is exposed to an alginate oligomer prior to an exposure to the composition comprising blood plasma in such a way that the alginate oligomer persists on the surface for a duration sufficient to prevent or inhibit blood coagulation on or at the treated surface. Preferably the alginate oligomer will persist for substantially the useful life of the surface, e.g. the pretreatment results in a substantially permanent coating of an alginate oligomer. However, a permanent anticoagulant effect is not necessary and it may be useful to provide a product or device with an anticoagulant effect of more limited duration, e.g., days, weeks or months. Thus a pretreated surface/product is one to which the alginate oligomer is applied and on which it remains. Such a product/surface may be a coated and/or impregnated product/surface. In certain embodiments a coating will comprise a plurality, i.e. at least two, layers of alginate oligomer. In other embodiments the alginate oligomer may be provided in a single layer, and in still other embodiments it may be end-attached, such that the alginate oligomer is more freely available to contact the plasma-containing composition.

Pretreatment can be achieved by any convenient means, for example any form of applying the alginate oligomer to the surface, notably coating the surface, e.g. spray drying, polymer coating with a polymer incorporating the alginate oligomer. Alternatively, the alginate oligomer can be incorporated or impregnated into the material from which the object or its susceptible parts are manufactured. This approach is suited to objects, or constituent parts thereof, manufactured from polymers such as plastics and silicones. Blood collection and storage products and dialysis/plasmapheresis products comprising an inanimate surface comprising an alginate oligomer coating or coating composition, or incorporating, or impregnated with, an alginate oligomer are therefore contemplated.

The in vitro/ex vivo method of the invention may thus comprise preparing a product or device having a reduced capacity to promote blood coagulation. The term "reduced capacity to promote blood coagulation" may be interpreted analogously with the definition of "prevention or inhibition of blood coagulation" given above. As discussed previously, an artificial surface has a propensity to induce coagulation, and most synthetic plastics, polymers and metal surfaces are thrombogenic. Alginate oligomers may be used according to the present invention to reduce that propensity, or capacity. More particularly, the alginate oligomer may reduce the extent of coagulation (or clot formation) induced by the product or device when placed in contact with a composition comprising blood plasma, e.g. blood or a blood-derived product, including when the product or device is placed in situ in a human or non-human animal body.

The induction of coagulation by medical devices represents a significant problem and, as noted above, any reduction in the rate and/or extent of coagulation is beneficial, even if small (e.g. at least 5 or 10% reduction).

An artificial surface may be any inanimate surface, and in particular a surface of a product of device intended to come into contact with a composition comprising blood plasma. In a particular embodiment it is a surface of or in a medical device. It may be any synthetic surface, e.g. polymer, plastic, rubber, silicone, metal or glass etc.

The preparation of a product or device having a reduced capacity to promote coagulation may involve a step of providing an alginate oligomer at or on a surface of said product or device, notably at or on an artificial surface. As noted and discussed above, the alginate oligomer may be incorporated or impregnated into the material from which the surface is made or formed, or it can be applied to the surface, most notably by coating.

The alginate oligomer may be applied (e.g. coated) by itself, or in combination with one or more other materials or components. Thus the alginate oligomer may be attached, or immobilised to the surface directly (by covalent or non-covalent attachment e.g. adsorption) or it may be incorporated into or contained within (e.g. entrapped in, or attached to) a material which is applied (e.g. coated) to the product or device, which material may itself be covalently or non-covalently attached. Thus by way of example, the alginate oligomer may be entrapped in a polymer or coating applied to the surface, or it may be covalently attached to a matrix polymer used to prepare a polymer coating. The polymer coating may be designed to provide for delayed release of the alginate oligomer, for example by incorporating it (e.g. entrapping it) in different polymer layers. Such delayed release may be over different time periods e.g. from days to months.

A number of different coating technologies for medical devices and such like are known, for example from SurModics, and any such technology may be used. Indeed, as noted above, it is known to provide medical devices and products with haemocompatible coatings to try to reduce coagulation. "Haemocompatible" is defined herein to mean that that the surface/material/product/device/coating or compound etc. in question does not elicit any negative response when placed in contact with blood or with a composition comprising plasma, or that any such negative response is reduced or inhibited e.g. minimised. A negative response may be coagulation, platelet activation etc., and in particular any response that can lead to, or increase, coagulation.

A haemocompatible material or coating may be "active", i.e. it may comprise bioactive agents which inhibit or prevent coagulation, for example by inhibiting thrombin generation (e.g. heparin), or it may be "passive", and may provide an anticoagulant or haemocompatible effect by e.g. shielding the surface from the blood, or reducing its capacity to induce coagulation, for example by reducing protein adsorption to the surface from the blood, and/or platelet activation. A passive coating may be viewed as "disguising" or "camouflaging" the surface so that it is not recognised as foreign in the blood. Various different active and passive haemocompatible coatings are known in the art. An alginate oligomer may be used in combination with such coatings and may be used to impart an active and/or a passive effect.

Thus, the alginate oligomer may be provided as part of, or included in, a haemocompatible coating, and may be used in combination with one or more haemocompatible compounds as discussed above, including both bioactive agents which may have an anticoagulant effect, e.g. heparin, hyaluronan, dextran etc. and polymers and/or plastics which may have a passive haemocompatible effect.

A further example of a haemocompatible compound is a molecule which may release nitric oxide (NO), which is known to prevent platelet activation. NO-releasing polymers have been developed.

The invention will be further described with reference to the following non-limiting Examples.

EXAMPLES

Example 1

Effect of G-Block Alginate Oligomers on the Coagulation Time of Whole Human Blood Materials and Methods
Test Materials and Controls The alginate oligomer tested was OligoG CF-5/20, a G-block alginate oligomer (DP 5 to 20, average molecular weight 2600, 90-95% G residues). OligoG was provided by AlgiPharma AS, Norway. Positive control was Fuller's Earth, Mesh size 8-16, Sigma-Aldrich A/S.

OligoG Formulation

A weighed sample of OligoG was sprinkled slowly in small amounts into sterile water (Fresenius Kabi AG, Germany) that was stirred magnetically. When the entire sample had been added, the stirring was continued for a further 50 minutes and additional sterile water was added to give the appropriate total final volume. The formulation quickly blocked a Sartorius MiniSart filter (0.2 μm pore size), so it was stored at room temperature overnight and then stirred magnetically for a further hour. It was still not possible to filter the formulation, so it was used in the test without filtration.

The final concentration of the OligoG formulation was 200 mg/ml, expressed in terms of the dry matter content (stated to be 95.2% in the OligoG sample supplied).

Coagulation Test Procedure

Aliquots (53 μl and 111 μl) of the OligoG formulation at 200 mg/mL were placed into separate test tubes. Fuller's Earth (ca. 100 mg/tube) was placed into positive control tubes. Empty tubes were also prepared as negative (untreated) controls.

Fresh blood samples were obtained by venepuncture of four healthy adult humans. The blood samples were collected from each donor using Liquidraw tubes (plain plastic). As each sample of blood was collected, aliquots (1 ml) were added within a few seconds of collection to each of the tubes to cover the test and control items. The OligoG formulation was mixed with blood at 5 and 10% v/v and thus the final concentrations of the OligoG in the mixtures were 10 and 20 mg/m (expressed in terms of the OligoG dry matter content). One tube containing each concentration of the OligoG and one tube with each control were tested with the blood from each donor. Immediately, the tubes were placed in a water bath at approximately 37° C. and shaken until coagulation occurred. The gentle shaking of the non-coagulated samples was continuous for ca. 20 to 30 minutes, then every ca. 5 to 10 minutes, and then less frequently. The time taken between the collection of the blood aliquot and complete coagulation was recorded for each tube.

Results

TABLE 1

Coagulation times for 4 different human blood samples in the presence of OligoG at 10 mg/ml or 20 mg/ml

| Treatment | Coagulation time (s—seconds; h = hours) | | | | | |
|---|---|---|---|---|---|---|
| | Donor 1 | Donor 2 | Donor 3 | Donor 4 | Mean ± S.D. | % of control |
| Negative control | 481 s | 428 s | 660 s | 615 s | 546 ± 109 s | 100 |
| Positive control | 222 s | 200 s | 207 s | 204 s | 208 ± 10 s | 38 |
| OligoG 20 mg/ml | >5 h[a] | >5 h[a] | >5 h[a] | >5 h[a] | — | — |
| OligoG 10 mg/ml | >5 h[a] | 3986 s to 6671 s[b] | >5 h[a] | >5 h[a] | — | >931 |

Key to Table 1:
% of control Mean coagulation time as a percentage of the mean negative control time
S.D. Standard deviation
Negative control Untreated
Positive control Treatment with Fuller's Earth
OligoG Treatment with OligoG CF-5/20
[a]Mixture remained un-coagulated
[b]Mixture coagulated sometime between these two observation points The positive control treatment with Fuller's Earth caused a large reduction in the mean coagulation time to 38% of the mean negative control value, demonstrating the efficacy and sensitivity of the test.

The mean coagulation time for the four untreated blood samples was 546 seconds. Treatment with OligoG at 10 mg/ml increased the coagulation time for the blood from one donor by a factor of greater than 9.31: coagulation occurred between observations at 3986 and 6671 seconds. The mixtures containing the test item at 10 mg/ml for the three other donors and at 20 mg/ml for all four donors remained un-coagulated more than five hours (>18000 seconds) after they were prepared and no further observations of the mixtures were made.

Conclusion

It is concluded that OligoG CF-5/20, and by extension alginate oligomers in general, is able to significantly inhibit, if not prevent, coagulation of whole human blood. On this evidence the use of alginate oligomers as anticoagulants both in vitro, e.g. in the handling of blood and blood products and in vivo, e.g. in anticoagulant therapy, may be proposed.

Example 2

Effect of M-Block and MG-Block Alginate Oligomers on the Coagulation Time of Whole Human Blood Materials and Methods
Test Materials and Controls The alginate oligomers tested were an M-block alginate oligomer (DPn 10, 100% M residues) and an MG-block alginate oligomer (DPn 15, essentially entirely an alternating sequence of M and G residues). Alginate oligomers were provided by AlgiPharma AS, Norway. Positive control was Fuller's Earth, Mesh size 8-16, Sigma-Aldrich A/S. Reference item was heparin LEO 5000 IE/ml, LEO Pharma A/S.

Formulation of Test Materials and Controls

A weighed sample of each oligomer (200 mg for M-blocks DPn10 and 200.1 mg for MG-blocks DPn 15) was sprinkled slowly in small amounts into sterile distilled water (880 µl, Fresenius Kabi AG, Germany) that was stirred magnetically. When the entirety of each test item had been added, the stirring was continued for a further 92-95 minutes until each test item had dissolved. The final concentration of each test item formulation was 200 mg/ml, expressed in terms of the test item sample supplied, and assuming that the displacement of the test item was 0.6 ml/g. The test item formulations were then stored at room temperature until use in the coagulation test on the following day.

Dilutions of the reference item were prepared in sterile distilled water (Fresenius Kabi AG, Germany) on the day of the coagulation test to give final Heparin concentrations of 200, 20 and 2 IU/ml.

Coagulation Test Procedure

Aliquots (53 µl and 111 µl) of each alginate oligomer formulation at 200 mg/ml were placed into separate test tubes. Aliquots (53 µl) of the reference item formulations at 200, 20 and 2 IU/ml were placed into separate test tubes. Fuller's Earth (ca. 100 mg/tube) was placed into positive control tubes. Empty tubes were also prepared as negative (untreated) controls.

Fresh blood samples were obtained by venepuncture of four healthy adult people. The blood samples were collected from each donor using Liquidraw tubes (plain plastic). As each sample of blood was collected, aliquots (1 ml) were added within a few seconds of collection to each of the tubes to cover the test alginate oligomers, reference and control items. The alginate oligomer formulations were mixed with blood at 5 and 10% v/v and thus the final concentrations of each alginate oligomer in the mixtures were 10 and 20 mg/ml (expressed in terms of the alginate oligomer samples as received). Each dilution of the reference item was mixed with blood at 5% v/v and thus the final concentrations of the reference item (heparin) in the mixtures were 10, 1 and 0.1 IU/ml. One tube containing each concentration of each test oligomer, one tube containing each concentration of the reference item and one tube with each control were tested with the blood from each donor. Immediately, the tubes were placed in a water bath at approximately 37° C. and shaken regularly until coagulation occurred. The time taken between the collection of the blood aliquot and complete coagulation was recorded for each tube. Samples that remained uncoagulated more than six or seven hours after the start of treatment were discarded at that time and no further observations were made.

Results

TABLE 2

Coagulation times for 4 different human blood samples in the presence of M-block alginate oligomers (DPn 10) and MG-block alginate oligomers (DPn 15) at 10 mg/ml or 20 mg/ml; heparin at 10, 1 and 0.1 IU/ml and Fuller's earth.

| Treatment | Donor 1 | Donor 2 | Donor 3 | Donor 4 | Mean ± S.D.[a] | % of control |
|---|---|---|---|---|---|---|
| Negative control | 921 s | 933 s | 938 s | 1046 s | 960 ± 58 s | 100 |
| Positive control | 257 s | 270 s | 219 s | 289 s | 259 ± 30 s | 27 |
| Test item A 20 mg/ml | 5035 s | 2295 s | >6 hb | 10259 s | >5863 ± 4046 s | >611 |
| Test item A 10 mg/ml | 2327 s | 2674 s | 1607 s | 2189 s | 2199 ± 444 s | 229 |
| Test item B 20 mg/ml | >7 hb | >7 hb | >6 hb | >6 hb | — | — |
| Test item B 10 mg/ml | 3359 s | 8331 s | 4473 s | 10850 s | 6753 ± 3464 s | 703 |
| Heparin 0.1 IU/ml | 1594 s | 1168 s | 2388 s | 1365 s | 1629 ± 535 s | 170 |

TABLE 2-continued

Coagulation times for 4 different human blood samples in the presence of M-block alginate oligomers (DPn 10) and MG-block alginate oligomers (DPn 15) at 10 mg/ml or 20 mg/ml; heparin at 10, 1 and 0.1 IU/ml and Fuller's earth.

| | Coagulation time (s = seconds; h = hours) | | | | | |
|---|---|---|---|---|---|---|
| Treatment | Donor 1 | Donor 2 | Donor 3 | Donor 4 | Mean ± S.D.[a] | % of control |
| Heparin 1 IU/ml | >7 hb | >7 hb | >6 hb | >6 hb | — | — |
| Heparin 10 IU/ml | >7 hb | >7 hb | >6 hb | >6 hb | — | — |

Key to Table 2:
% of control Mean coagulation time as a percentage of the mean negative control time
S.D. Standard deviation
[a]All mean and S.D. exclude values from un-coagulated samples
bMixture remained un-coagulated
Negative control Untreated
Positive control Treatment with Fuller's Earth
Test item A M-block alginate oligomer DPn 10
Test item B MG-block alginate oligomer DPn 15

The positive control treatment with Fuller's Earth caused a large reduction in the mean coagulation time to 27% of the mean negative control value, demonstrating the efficacy and sensitivity of the test.

Treatment with the M-block alginate oligomer (DPn 10) delayed coagulation at both concentrations tested and in blood samples from all four donors. At 10 mg/ml, the mean coagulation time showed an increase to 229% of the mean negative control value. At 20 mg/ml, the mean coagulation time for three of the donors showed an increase to 611% of the mean negative control value, while the blood sample from the fourth donor remained uncoagulated more than six hours after the start of treatment.

Treatment with the MG-block alginate oligomer (DPn 15) delayed coagulation at both concentrations tested and in blood samples for all four donors. The effect was greater than that caused by the M-block alginate oligomer: at 10 mg/ml the MG block alginate oligomer increased the mean coagulation time to 703% of the mean negative control value. At 20 mg/ml, the blood samples from all four donors remained uncoagulated more than six or seven hours after the start of treatment. This is effect is lower than that caused by the G-block alginate oligomer where blood from all but one donor remained uncoagulated after 5 hours at 10 mg/ml or 20 mg/ml of G-block alginate oligomer The reference item, heparin, delayed coagulation at all three concentrations tested and in blood samples for all four donors. At 0.1 IU/ml, the mean coagulation time was increased to 170% of the mean negative control value. At 1 and 10 IU/ml, the blood samples from all four donors remained uncoagulated more than six or seven hours after the start of treatment. Thus, the effect on coagulation time of M-block and MG-block alginate oligomers at 10 mg/ml was equivalent to the effect of heparin at between 0.1 and 1 IU/ml.

Conclusion

It is concluded that both M-block alginate oligomers and MG-block alginate oligomers caused marked increases in the coagulation time of blood from all four donors. The effect of both M-block alginate oligomers and MG-block alginate oligomers at 10 mg/ml was equivalent to the effect of heparin at between 0.1 and 1 IU/ml.

The effect of the MG-block alginate oligomer was greater than that of the M-block alginate oligomer, but less than the G-block alginate oligomer of Example 1. Thus, different uronic acid monomer sequences and/or different oligomer lengths may have different degrees of anticoagulant effect and thus appropriate selection of alginate oligomers may allow particular degrees of anticoagulation to be achieved in particular scenarios. For instance, a greater amount of G residues and/or length of G block may be selected to give a more potent anticoagulation effect.

What is claimed is:

1. An in vitro or ex vivo method for the prevention or inhibition of blood coagulation, said method comprising contacting a composition comprising blood plasma or a material with which said composition is, or may be, in contact, with an alginate oligomer, wherein said alginate oligomer contains 2 to 75 monomer residues of which at least 30% are guluronic acid residues, and wherein said monomer residues do not carry a sulfate group.

2. The in vitro or ex vivo method of claim 1, wherein said composition comprising blood plasma is whole blood.

3. The in vitro or ex vivo method of claim 1, wherein said composition comprising blood plasma is sterile.

4. The in vitro or ex vivo method of claim 1, wherein the material is, or is part of, a product or device which in use comes into contact with blood or a blood-derived product.

5. The in vitro or ex vivo method of claim 1, wherein said method is for preparing a product or device having a reduced capacity to promote blood coagulation, said method comprising providing the alginate oligomer at or on a surface of said product or device.

6. The in vitro or ex vivo method of claim 1, wherein the alginate oligomer is incorporated or impregnated in the material, or applied to a surface of the material which comes into contact with the composition.

7. The in vitro or ex vivo method of claim 1, wherein the alginate oligomer is coated onto a surface of the material, or provided as part of a surface coating.

8. The in vitro or ex vivo method of claim 7, wherein the alginate oligomer is provided or included in a hemocompatible coating comprising one or more further hemocompatible compounds.

9. The in vitro or ex vivo method of claim 1, wherein the material is selected from the group consisting of:
   (i) a sterile blood collection vessel or conduit,
   (ii) a dialysis or plasmapheresis consumable or a piece of dialysis or plasmapheresis equipment or machinery,
   (iii) an implantable medical, surgical or prosthetic device,
   (iv) a transplant tissue, and
   (v) a diagnostic product or device, or a part thereof.

10. The in vitro or ex vivo method of claim 9 wherein
(i) said implantable medical, surgical or prosthetic device is a catheter, a heart valve, a vascular stent, an artificial joint, an intrauterine device, a pacemaker, a tracheostomy tube, a radiotherapy wire or a soft tissue implant,
(ii) said transplant tissue is heart, lung, kidney, liver, pancreas, intestine or corneal tissue, an arterial or venous graft or skin, and
(iii) said dialysis or plasmapheresis consumable, or piece of dialysis or plasmapheresis equipment or machinery is a dialysis or plasmapheresis conduit, receptacle or filter.

11. The in vitro or ex vivo method of claim 9 wherein said material contains or carries an alginate oligomer at or on a surface with which a composition comprising blood plasma may come into contact, optionally wherein said surface also contains or carries one or more further hemocompatible compounds.

12. The method according to claim 1, wherein the alginate oligomer has a number average degree of polymerization of 2 to 50.

13. The method according to claim 1, wherein the alginate oligomer is a 2- to 35-mer.

14. The method according to claim 1, wherein the alginate oligomer has at least 70% G residues.

15. The method according to claim 14, wherein at least 80% of the G residues are arranged in G-blocks.

16. The method according to claim 1, wherein at least 80% of the M residues are arranged in M blocks.

17. The method according to claim 1, wherein at least 70% of the G and M residues in the oligomer are arranged in MG blocks.

18. The in vitro or ex vivo method of claim 8, wherein the further hemocompatible compound is selected from the group consisting of heparin, heparan sulfate, hyaluronan, polyethylene glycol and dextran.

19. The in vitro or ex vivo method according to claim 10, wherein the heart transplant tissue is heart valve.

20. The in vitro or ex vivo method according to claim 11, wherein the further hemocompatible compound is selected from the group consisting of heparin, heparan sulfate, hyaluronan, polyethylene glycol and dextran.

21. The method according to claim 1, wherein the alginate oligomer is in a non-immobilized form.

22. The method according to claim 1, wherein at least 80% of the M residues are arranged in M blocks.

23. The method according to claim 1, wherein the alginate oligomer has 50-95% G residues.

24. The method according to claim 1, wherein the alginate oligomer has 90-95% G residues.

25. A method for treating or inhibiting thrombosis or treating a disease or condition associated with blood coagulation in a subject in need thereof comprising administering to the subject an alginate oligomer by topical, enteral or parenteral routes or by inhalation, wherein said alginate oligomer contains 2 to 75 monomer residues of which at least 30% are guluronic acid residues, and wherein said monomer residues do not carry a sulfate group.

26. The method according to claim 25, wherein said disease or condition is venous thrombosis, arterial thrombosis, atherosclerosis, vein graft failure, arterial graft failure, stroke, cardiac infarction, pulmonary embolism or thrombophilia.

27. The method according to claim 25, wherein said alginate oligomer is administered to a subject:
(i) that will be or is immobile for prolonged periods,
(ii) with arterial fibrillation,
(iii) with an atherosclerotic plaque,
(iv) with or receiving an implantable medical, surgical or prosthetic device,
(v) undergoing, about to undergo or recovering from a surgical procedure, and/or
(vi) with congenital or acquired thrombophilia.

28. The method according to claim 25, wherein the formation of thromboses on a surface of a material selected from the group consisting of an implantable or in-dwelling medical, surgical or prosthetic device, a transplant tissue, a dialysis or plasmapheresis consumable and a piece of dialysis or plasmapheresis equipment or machinery is inhibited or prevented.

29. The method according to claim 25, wherein said alginate oligomer is for use before, during and/or after a surgical procedure to inhibit or prevent the formation of thromboses at sites of surgical incision.

30. The method according to claim 25, wherein the alginate oligomer is in a non-immobilized form.

31. The method according to claim 25, wherein the alginate oligomer has a number average degree of polymerization of 2 to 50.

32. The method according to claim 25, wherein the alginate oligomer is a 2- to 35-mer.

33. The method according to claim 25, wherein the alginate oligomer has at least 70% G residues.

34. The method according to claim 33, wherein at least 80% of the G residues are arranged in G-blocks.

35. A method for treating or inhibiting thrombosis or treating a disease or condition associated with blood coagulation in a subject undergoing dialysis or plasmapheresis, said method comprising:
(i) providing an extracorporeal dialysis or plasmapheresis consumable which contains or carries an alginate oligomer at or on a surface with which blood or plasma may come into contact, or an extracorporeal piece of dialysis or plasmapheresis equipment or machinery which contains or carries an alginate oligomer at or on a surface with which blood or plasma may come into contact, and
(ii) performing dialysis or plasmapheresis on said subject with said consumable, piece of equipment or machinery,
wherein said alginate oligomer contains 2 to 75 monomer residues of which at least 30% are guluronic acid residues, and said monomer residues do not carry a sulfate group.

* * * * *